(12) United States Patent
Bennett

(10) Patent No.: US 10,490,904 B2
(45) Date of Patent: Nov. 26, 2019

(54) DEVICE FOR DETECTING PRECIPITATION CONDITIONS

(71) Applicant: Bristol Industrial and Research Associates Limited, Portishead, Bristol (GB)

(72) Inventor: Alec Bennett, Bristol (GB)

(73) Assignee: Bristol Industrial and Research Associates Limited, Portishead, Bristol (GB)

(*) Notice: Subject to any disclaimer, the term of this patent is extended or adjusted under 35 U.S.C. 154(b) by 366 days.

(21) Appl. No.: 15/400,834

(22) Filed: Jan. 6, 2017

(65) Prior Publication Data
US 2017/0214149 A1  Jul. 27, 2017

(30) Foreign Application Priority Data
Jan. 22, 2016 (EP) .................................. 16152358

(51) Int. Cl.
*H01Q 19/30* (2006.01)
*G01W 1/14* (2006.01)
(Continued)

(52) U.S. Cl.
CPC ............. *H01Q 19/30* (2013.01); *G01N 22/04* (2013.01); *G01W 1/14* (2013.01); *H01Q 21/30* (2013.01);
(Continued)

(58) Field of Classification Search
CPC .......... H01Q 11/08; H01Q 1/02; H01Q 1/084; H01Q 1/12; H01Q 1/2216; H01Q 1/3275; H01Q 1/36; H01Q 21/28; H01Q 11/12; H01Q 19/30; H01Q 21/29; B60R 21/0134; B60R 21/0153; G01S 17/89; G01S 13/931; G01S 2013/9357; G01S 7/539;
(Continued)

(56) References Cited

U.S. PATENT DOCUMENTS 3,665,466 A * 5/1972 Hibbard ................. G01B 15/02
                                                          324/330
4,633,256 A * 12/1986 Chadwick ............. G01S 13/951
                                                          342/368
(Continued)

OTHER PUBLICATIONS

Extended European Search Report dated Jul. 7, 2016 in corresponding European Application No. 16152358.4, filed Jan. 22, 2016 (in 8 pages).

*Primary Examiner* — Olumide Ajibade Akonai
(74) *Attorney, Agent, or Firm* — Knobbe Martens Olson & Bear, LLP

(57) ABSTRACT

Provided is a device for detecting precipitation conditions. In one aspect, the device includes a Yagi-Uda antenna tuned a resonant frequency and a signal generator coupled to the Yagi-Uda antenna by a transmission line, the signal generator being configured to output an excitation signal to the Yagi-Uda antenna to the Yadi-Uda antenna. The device also includes a processing system coupled to the Yagi-Uda antenna, the processing system being configured to measure the ability of the Yagi-Uda antenna to radiate a signal following excitation of the Yagi-Uda antenna by the excitation signal and, based on the measured ability of the Yagi-Uda antenna, to identify a precipitation or other meteorological condition.

11 Claims, 13 Drawing Sheets

(51) Int. Cl.
    *H04B 17/10*    (2015.01)
    *H01Q 21/30*    (2006.01)
    *G01N 22/04*    (2006.01)
    *H01Q 1/12*     (2006.01)
    *H01Q 1/02*     (2006.01)
(52) U.S. Cl.
    CPC ............. *H04B 17/103* (2015.01); *H01Q 1/02*
                    (2013.01); *H01Q 1/12* (2013.01)
(58) Field of Classification Search
    CPC ........ G01S 2007/4975; G06K 9/00624; G06K
                                    9/00805; B60W 30/16
    See application file for complete search history.

(56) References Cited

U.S. PATENT DOCUMENTS

| | | | |
|---|---|---|---|
| 6,753,806 B1* | 6/2004 | Hager | G01S 13/53 |
| | | | 342/120 |
| 6,856,273 B1 | 2/2005 | Bognar | |
| 7,376,404 B2* | 5/2008 | Lehnert | H04B 17/21 |
| | | | 455/132 |
| 9,116,241 B2 | 8/2015 | Bechler | |
| 9,476,977 B2* | 10/2016 | Lim | G01S 13/956 |
| 2003/0034912 A1* | 2/2003 | Williams | G01S 13/56 |
| | | | 342/28 |
| 2007/0229386 A1* | 10/2007 | Mertel | H01Q 3/12 |
| | | | 343/823 |
| 2011/0267219 A1* | 11/2011 | Kisliansky | G01S 7/414 |
| | | | 342/90 |

* cited by examiner

DEVICE FOR DETECTING PRECIPITATION CONDITIONS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present application relates to a device for detecting precipitation conditions and other meteorological conditions.

Description of the Related Art

Adverse precipitation conditions can have a significant negative impact on activities performed by individuals and organisations. One such adverse precipitation condition is freezing rain, which arises when liquid rain drops are supercooled as they fall, and subsequently freeze on contact with a surface, resulting in a coating of ice on the surface. Freezing rain can cause a wide range of problems, from increasing the risk of personal injury due to slipping or road traffic accidents, to dangerous build-up of ice on aircraft and damage to trees, roofs, power cables, pylons, wind turbines and other structures due to the weight of accumulated ice. Thus, prompt and reliable detection of freezing rain and other adverse weather conditions is required by national weather services, transportation, power and civil protection authorities.

Known methods for detecting ice involve either emitting or receiving near infra-red radiation for remote detection, continuous assessment of the resonant frequency of a protruding metallic probe, or detection of changes in the capacitance of an exposed surface.

Whilst all of these methods have been shown to work, all have disadvantages. For example, using near infra-red remote detection will only provide a yes/no result and not a quantitative estimation of ice thickness or accumulation rate. Additionally, near infra-red solutions require line of sight, meaning that any windows between the infra-red emitter and receiver will need to be clean and clear of contamination including drifting snow.

Resonant frequency probes typically offer a relatively small surface area for precipitation to adhere to, and so there is a reduced probability of correct detection of freezing rain during light rainfall. Additionally, the cost of such probes can be prohibitive.

Capacitance based sensors typically also offer only a yes/no result, rather than providing any quantitative estimation of ice thickness or accumulation rate, and may be vulnerable to contamination and erroneous results, as the detection technique involves estimation of relative permittivity. Such sensors are typically able to detect water accurately, as the relative permittivity of water is around 80 times that of air. In contrast, the relative permittivity of ice is much lower, at around 3 times that of air, and so detection of ice may be less accurate, as a surface layer of contaminants on the sensor having a similar relative permittivity value may be incorrectly identified as ice.

Thus, a need exists for an accurate, cost effective and reliable device for detecting freezing rain and other precipitation conditions.

SUMMARY

According to a first aspect of the described technology, there is provided a device for detecting precipitation conditions, the device comprising: a Yagi-Uda antenna tuned a resonant frequency; a signal generator coupled to the Yagi-Uda antenna by a transmission line, the signal generator being configured to output an excitation signal to the Yagi-Uda antenna; and a processing system coupled to the Yagi-Uda antenna, the processing system being configured to measure the ability of the Yagi-Uda antenna to radiate a signal following excitation of the Yagi-Uda antenna by the excitation signal and, based on the measured ability of the Yagi-Uda antenna, to identify a precipitation or other meteorological condition.

The device of the described technology permits accurate, cost effective and reliable detection and identification of precipitation conditions.

The signal generator may be configured to generate an excitation signal containing a plurality of different signals, each of the plurality of different signals having a different frequency in a frequency range around the resonant frequency of the Yagi-Uda antenna.

Alternatively, the signal generator may be configured to generate an excitation signal that sweeps or steps through a frequency range around the resonant frequency of the Yagi-Uda antenna.

The processing system may be configured to measure a voltage standing wave ratio (VSWR) in the transmission line in order to measure power reflected by the Yagi-Uda antenna.

The processing system may be configured to analyse a VSWR spectrum of the Yagi-Uda antenna and to identify characteristic features in the VSWR spectrum to identify a precipitation condition.

The processing system may be configured to identify characteristic features that are indicative of the presence of rain, snow freezing rain, ice, frost and dew.

The processing system may be configured to analyse the VSWR spectrum over a period of time and to identify characteristic features of the VSWR spectrum to identity changes in the precipitation condition.

The excitation signal is preferably an unmodulated signal.

The excitation signal may have a power in the range of tens of microwatts to tens of milliwatts.

The device may further comprise a temperature sensor.

The temperature sensor may be located within the antenna.

The device may further comprise a second antenna configured to detect a signal radiated by the Yagi-Uda antenna, and the processing system may be configured to measure the power of the signal received by the second antenna and, based on the measured received power, to identify a precipitation or other meteorological condition.

The second antenna may be heated.

BRIEF DESCRIPTION OF THE DRAWINGS

Embodiments will now be described, strictly by way of example only, with reference to the accompanying drawings, of which.

DETAILED DESCRIPTION OF CERTAIN INVENTIVE EMBODIMENTS

Figure 1:
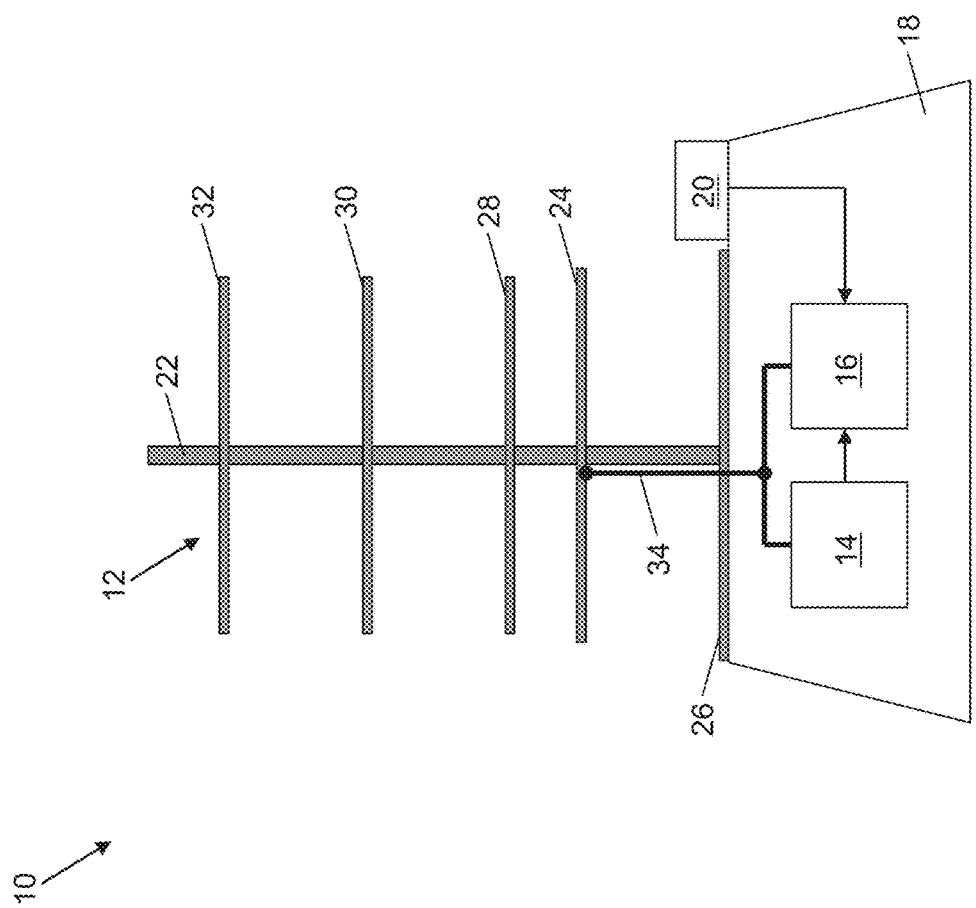
FIG. 1 is a schematic representation of a device for detecting precipitation conditions.

FIG. 1 is a schematic representation of a device for detecting weather conditions. The device, shown generally at 10 in FIG. 1, includes a tuned Yagi-Uda antenna 12 which is coupled to a signal generator 14 and to a processing system 16. In the example illustrated in FIG. 1 the signal generator 14 and the processing system 16 are located within a housing 18 on which the antenna 12 is mounted, but it will be appreciated by those skilled in the relevant art that the signal generator 14 and the processing system 16 need not be located within the housing 18, but may be located elsewhere as appropriate.

The device 10 may further include a temperature sensor 20, such as a thermocouple, positioned in close proximity to the Yagi-Uda antenna 12, for example on the housing 18, or within the structure of the antenna 12, and coupled to the processing system 16. The purpose of the temperature sensor 20 will be explained in detail below.

The Yagi-Uda antenna in the illustrated embodiment 12 includes a boom 22 on which a driven element 24, a reflector 26, and a plurality (in the example three) of directors 28, 30, 32 are mounted. In use of the device 10 the antenna 12 should preferably be mounted in a generally upright orientation as shown in FIG. 1, such that the boom 22 extends upwardly from a structure on which the device 10 is mounted. To prevent the device from being obscured or damaged by birds or other wildlife the device 10 may be provided with bird spikes, to discourage birds or other wildlife from alighting on or moving over the device.

The Yagi-Uda antenna 12 is tuned to resonate at a particular frequency. This tuning of the antenna is achieved at least in part by the size and configuration of the boom 22, driven element 24, reflector 26 and directors 28, 30, 32. It will be appreciated that the exact form of the Yagi-Uda antenna 12 may differ from that shown in FIG. 1, depending on the frequency to which the antenna 12 is tuned. In particular, the antenna 12 may include more or fewer reflectors and more or fewer directors than are shown in FIG. 1.

The driven element 24 of the antenna 12 is coupled to the signal generator 14 by an appropriate transmission line 34, such as coaxial cable. The signal generator 14 is configured to generate an excitation signal to excite the antenna 12. The excitation signal includes at least one unmodulated signal having a frequency that is substantially the same as the frequency to which the antenna 12 is tuned. Preferably, however, the excitation signal includes a plurality (e.g. at least two but not more than nine) of individual unmodulated signals, each individual signal having a different frequency in a frequency range around the frequency to which the antenna 12 is tuned. For example, if the antenna 12 is tuned to resonate at 2.4 GHz, the excitation signal may include one signal having a frequency of 2.4 GHz and a number of additional low power signals each having a different frequency in the range 1 GHz to 3 GHz.

Alternatively, the signal generator 14 may be configured to generate an excitation signal that sweeps or steps through a range of frequencies around the resonant frequency of the antenna 12. For example, the if the antenna 12 is tuned to resonate at 2.4 GHz, the signal generator 14 may be configured to generate an excitation signal that sweeps or steps through a frequency range of 1 GHz to 3 GHz.

The purpose of the antenna 12 is not to transmit a signal over a long range. Instead, the processing system 16 detects differences in the resonant frequency and/or input impedance of the antenna 12 arising from the presence on the antenna elements of water, ice, snow, frost, dew, condensation or the like resulting from prevailing precipitation conditions, by measuring the amount of the power of the excitation signal that is reflected or transmitted by the antenna 12. This does not require a high-power excitation signal, meaning that the excitation signal(s) can be low power, for example of the order of tens of microwatts to tens of milliwatts. The use of a low power excitation signal helps to minimise the power consumption of the device 10, but also, in conjunction with the use of unmodulated excitation signals, allows the device 10 to be operated without a license in many jurisdictions, and helps the device 10 to meet electromagnetic compliance requirements.

The signal generator 14 also outputs the excitation signal to the processing system 16. The processing system 16 is also coupled to transmission line 34. The processing system 16 is configured to measure the reflected power in the transmission line 34 resulting from excitation of the antenna 12 by the excitation signal, and, based on the measured reflected power, to identify a precipitation condition prevailing in the vicinity of the device 10, as will be explained in detail below.

The resonant frequency of the tuned Yagi-Uda antenna 12 is highly sensitive to changes in the thickness of the antenna elements 24, 26, 28, 30, 32, as the impedance of the antenna 12 changes as a result in the change of thickness of the antenna element(s). Even small changes in the thickness of one or more of the antenna elements 24, 26, 28, 30, 32, such as can be caused by the presence of rain, snow, condensation, dew, frost, ice or freezing rain can cause an appreciable deviation in the antenna's impedance and resonant frequency. The deviation in the impedance and resonant frequency of the antenna 12 causes the amount of reflected power in the transmission line 34, following excitation of the antenna 12 by the excitation signal, to change. The change in reflected power in the transmission line 34 is measured by the processing system 16, for example by measuring the voltage standing wave ratio (VSWR) in the transmission line 34, and, based on the measured change, the processing system 16 can identify a prevailing precipitation condition, as will now be explained by reference to FIGS. 2 to 12 of the accompanying drawings.

Figure 2:
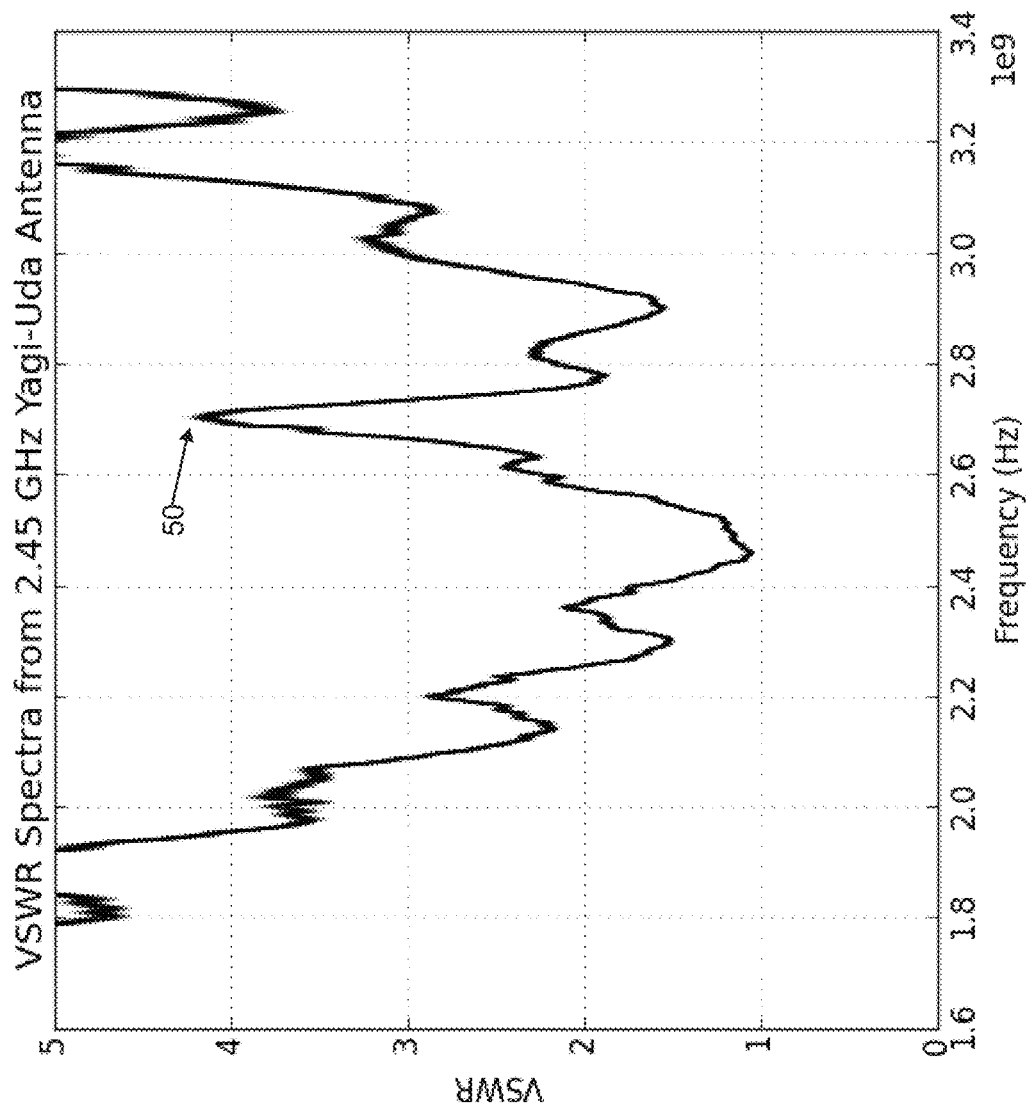
FIG. 2 is a voltage standing wave ratio (VSWR) spectrum for a dry antenna excited by an excitation signal.

FIG. 2 shows, at 50, an exemplary VSWR spectrum for an antenna of the kind illustrated in FIG. 1 tuned to a resonant frequency of 2.45 GHz when the antenna is dry (i.e. is unaffected by any precipitation) and is excited by an excitation signal containing a number of signals having frequencies in the range from approximately 1.7 GHz to approximately 3.3 GHz. As can be seen, when the antenna is dry, the VSWR approaches the ideal of 1 (indicating that none of the power of the excitation signal is reflected back to the source) for an excitation signal having a frequency of around 2.45 GHz, whilst there are peaks in VSWR at other frequencies. In the illustrated example, only 0.2% of the excitation signal power is reflected for an excitation signal having a frequency of 2.45 GHz, whilst for an excitation signal of around 2.7 GHz, the VSWR exceeds 4, indicating that around 37% of the transmitted power is reflected.

Figure 3:
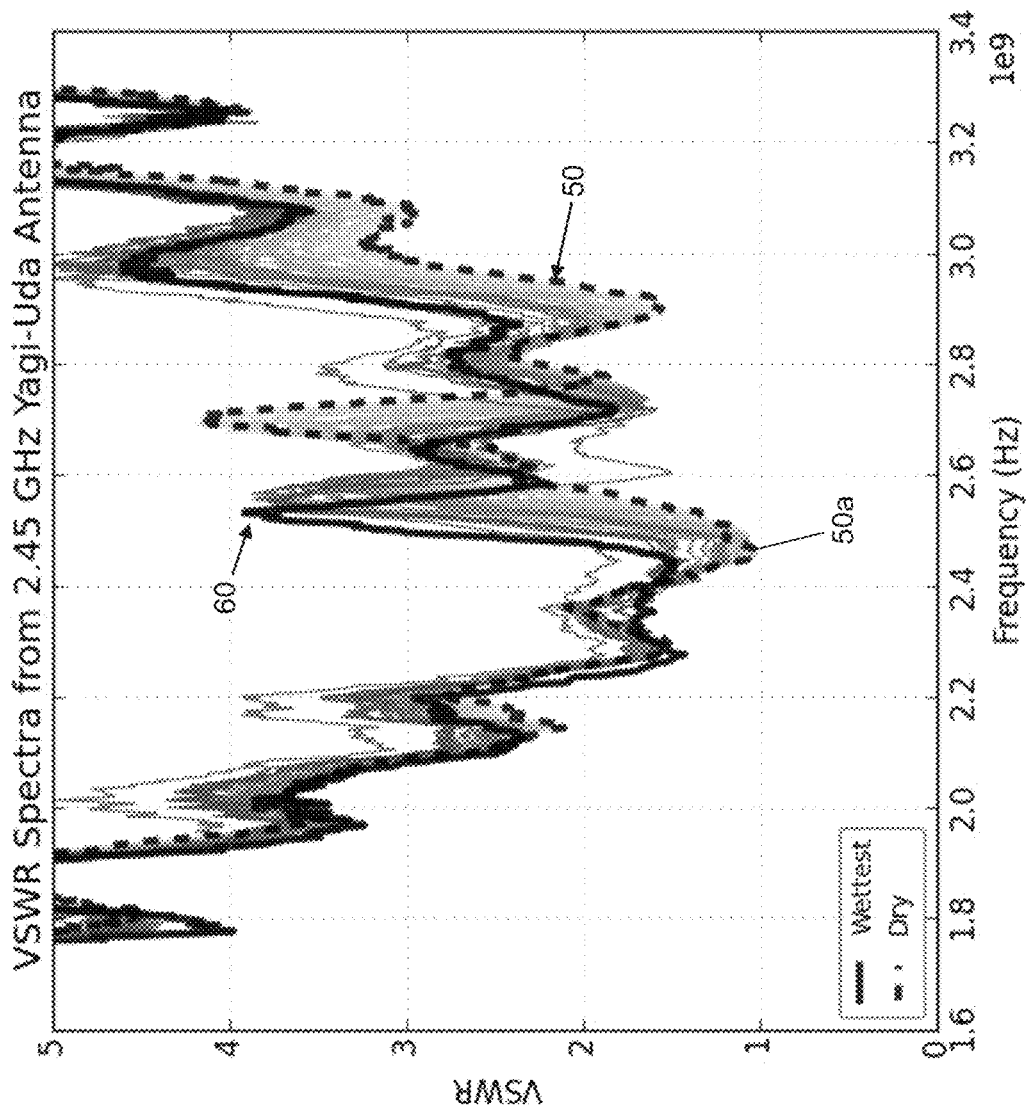
FIG. 3 is a VSWR spectrum for an antenna as the antenna becomes progressively wetter.

FIG. 3 is an exemplary VSWR spectrum for an antenna of the kind illustrated in FIG. 1 tuned to a resonant frequency of 2.45 GHz when the antenna has been wet with liquid water, in order to simulate the effect of rain, and excited by an excitation frequency containing a number of signals having frequencies in the range from approximately 1.7 GHz to approximately 3.3 GHz. The VSWR spectrum of the dry antenna shown in FIG. 2 is also shown at 50 in FIG. 3 for comparison purposes. A number of spectra are shown in FIG. 3 for the antenna as it becomes progressively wetter. The spectrum 60 is for the antenna at its wettest.

Figure 4:
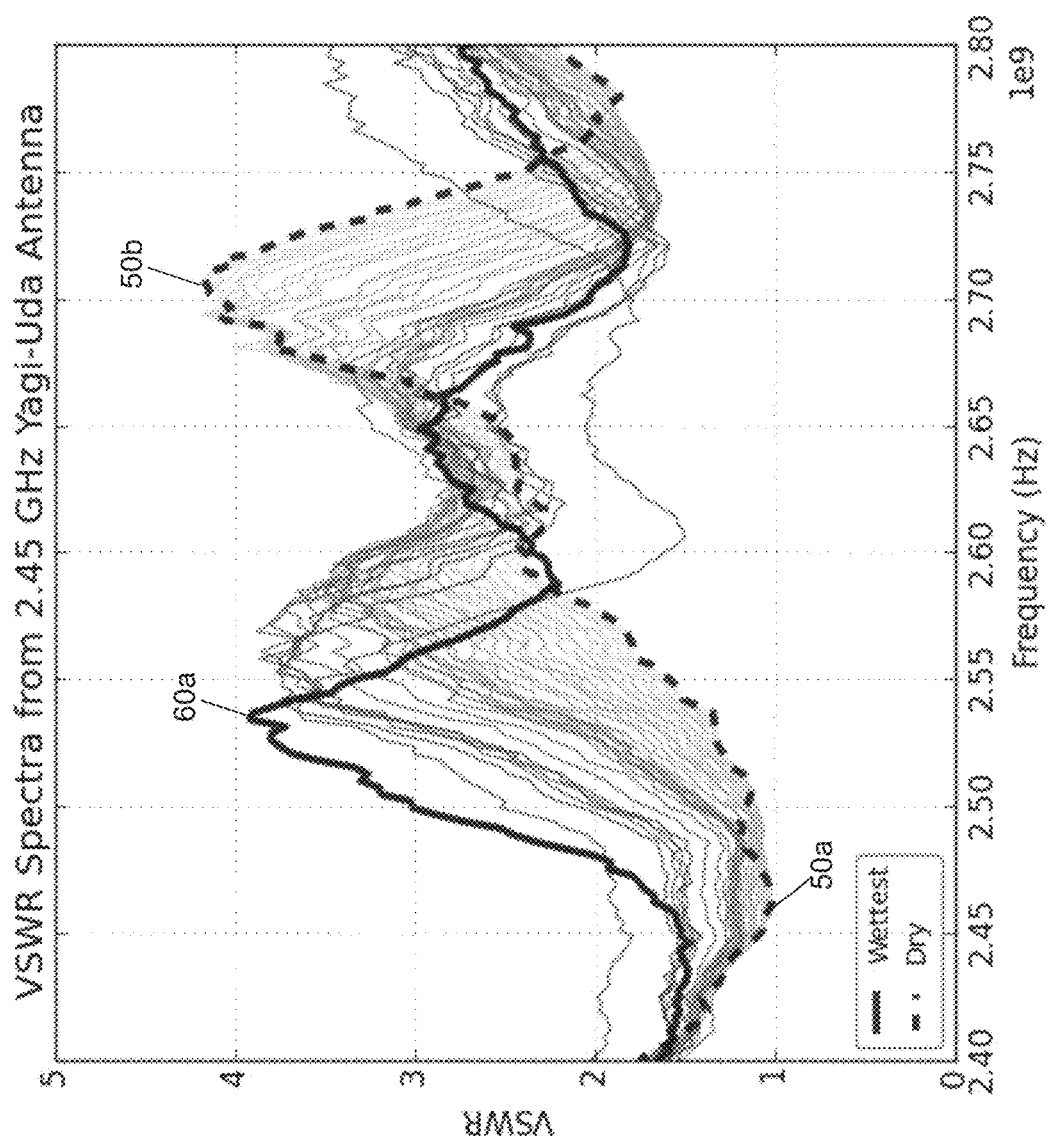
FIG. 4 is a more detailed view of the VSWR spectrum of FIG. 3.

As can be seen from FIG. 3, the VSWR spectrum when the antenna is wet is significantly different from the VSWR spectrum for the dry antenna, and includes regions (at input frequencies of around 2.0 GHz, just under 2.2 GHz and around 3 GHz) of increased reflection of input signal power, as compared to the VSWR spectrum for the dry antenna shown in FIG. 2, and a region (between around 2.4 GHz and 2.8 GHz, shown in magnified view in FIG. 4) of significant variability in VSWR.

As can be seen most clearly in FIG. 4, whilst the VSWR spectrum when the antenna is dry includes a minimum 50a at approximately 2.45 GHz, where the VSWR is slightly greater than 1, the VSWR for the wet antenna does not come as close to 1 anywhere in the input frequency range. Further, for the wet antenna there is a peak 60a in VSWR at an input frequency of approximately 2.54 GHz. There is no corresponding peak in the VSWR spectrum at this frequency for the dry antenna. On the other hand, there is a peak 50b in the VSWR spectrum for the dry antenna at around 2.70 GHz, with no corresponding peak in the VSWR spectrum at this frequency for the wet antenna.

The processing system 16 is configured to analyse the VSWR spectra of the antenna 12 and to identify characteristic features such as the minimum 50a and the peaks 50b, 60a to determine when the antenna 12 is wet, which may be indicative that the current precipitation condition is rain. Having identified that the current precipitation condition is rain the processing system 16 may output a signal, e.g. to a remote weather station, indicating that rain has been detected.

Figure 5:
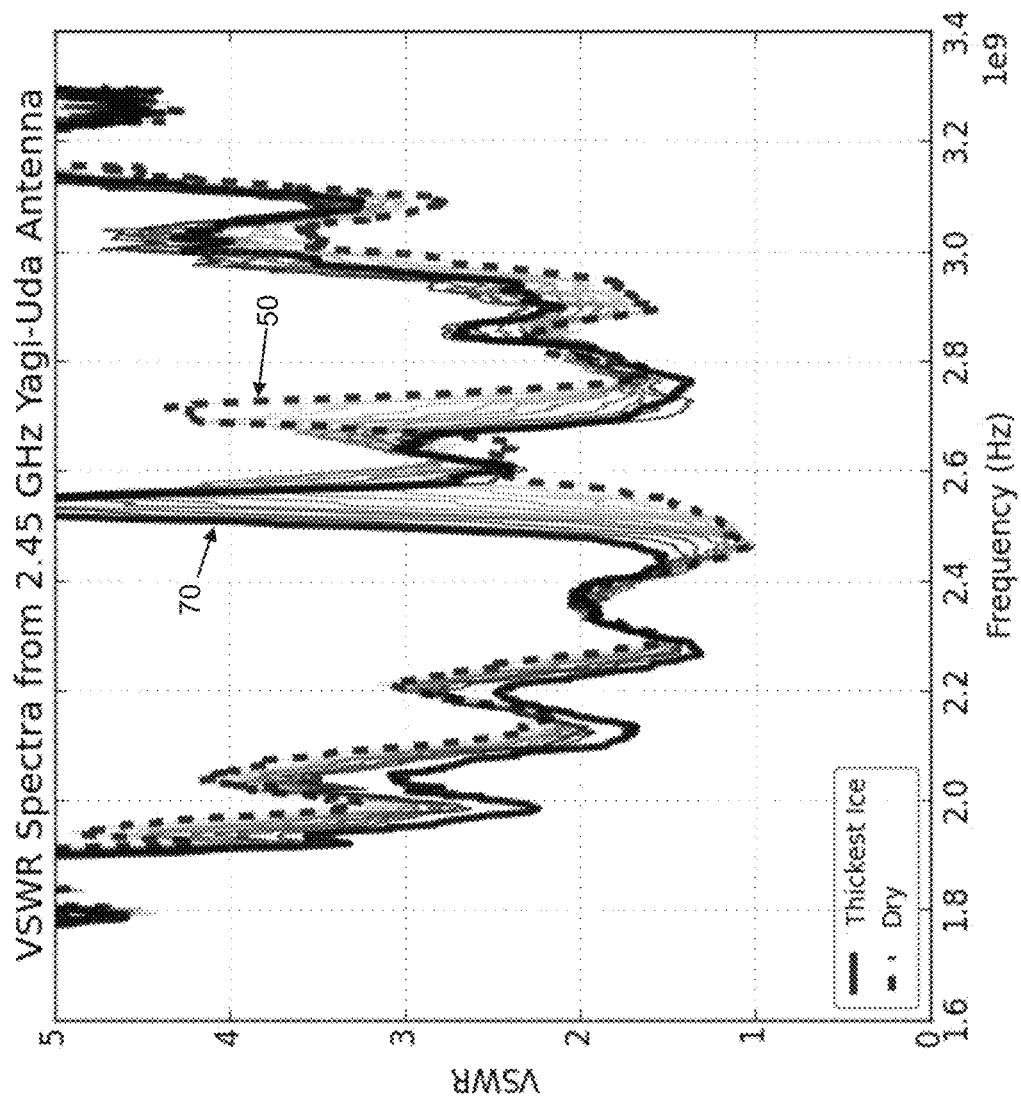
FIG. 5 is a VSWR spectrum for an antenna as the thickness of a coating of ice on the antenna increases.
Figure 6:
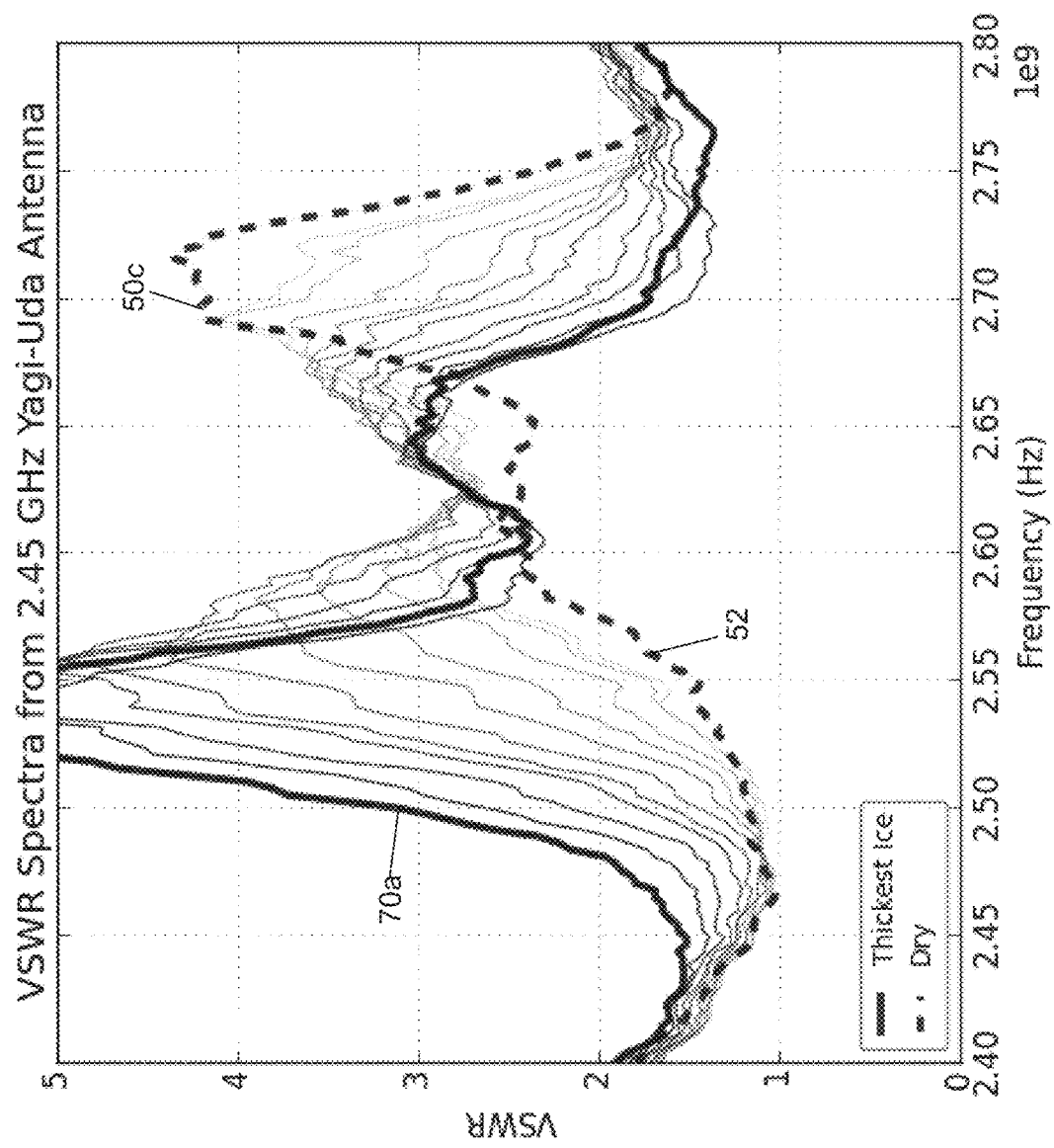
FIG. 6 is a more detailed view of the VSWR spectrum of FIG. 5.

FIG. 5 is an exemplary VSWR spectrum for an antenna of the kind illustrated in FIG. 1 tuned to a resonant frequency of 2.45 GHz when the antenna has been coated with ice by applying chilled water to the antenna after it has been cooled to approximately −4° C., in order to simulate the effect of a build-up of ice on the antenna, and excited by an excitation frequency containing a number of signals having frequencies in the range from approximately 1.7 GHz to approximately 3.3 GHz. The VSWR spectrum of the dry antenna shown in FIG. 2 is also shown at 50 in FIG. 5 for comparison purposes. A number of spectra are shown in FIG. 5 for the antenna as the coating of ice becomes thicker as more layers develop as more chilled water is applied. The spectrum 70 is for the antenna with the coating of ice at its thickest, corresponding to a radial thickness of ice of around 2 mm.

As can be seen from FIG. 5, the VSWR spectrum for the antenna when coated with ice is different from the VSWR spectrum for the dry antenna, and includes a regions (e.g. at input frequencies of around 2 GHz and around 2.2 GHz) of significantly decreased reflection of input signal power (i.e. reduced VSWR), as compared to the VSWR spectrum for the dry antenna shown in FIG. 2, and a region between around 2.4 and 2.8 GHz (shown in magnified view in FIG. 6) of significant variability in VSWR. These differences become more pronounced as the thickness of ice on the antenna increases. Additionally, as can be seen most clearly in FIG. 6, there is a peak 50c in the VSWR spectrum for the dry antenna at around 2.70 GHz, after which the VSWR remains generally stable until the input frequency reaches around 2.702 GHZ. In contrast, for all thicknesses of ice there is a peak in the VSWR spectrum at an input frequency of just under 2.70 GHz, after which the VSWR drops off sharply with increasing input frequency.

The processing system 16 is configured to analyse the VSWR spectra of the antenna 12 and to identify characteristic features, such as the regions of significantly decreased reflection of input signal power and the VSWR peak at just under 2.7 GHz followed by a sharp drop in VSWR with increasing input frequency, to determine when the antenna 12 has a coating of ice, which may be indicative that freezing rain is falling, or that the temperature has recently dropped below freezing. Having identified that this current condition, the processing system 16 may output an appropriate signal, e.g. to a remote weather station, indicating that ice has been detected.

In order to distinguish between a coating of ice on the antenna caused by freezing rain and a coating of ice caused by a drop in temperature causing a coating of water on the antenna to freeze, the processing system 16 may analyse temperature data from the temperature sensor 20 as well as the VSWR spectra of the antenna. For example, if the data from the sensor 20 indicates that the temperature has recently dropped to below freezing, the processing system may infer that the coating of ice on the antenna is due to this temperature drop, and may output a signal, e.g. to a remote weather station, indicating that freezing temperatures have been detected. On the other hand, if the coating of ice is not accompanied by a recent drop in temperature below freezing, the processing system 16 may infer that the coating of ice is a result of freezing rain, and may output a signal, e.g. to the remote weather station, indicating that freezing rain has been detected.

Figure 7:
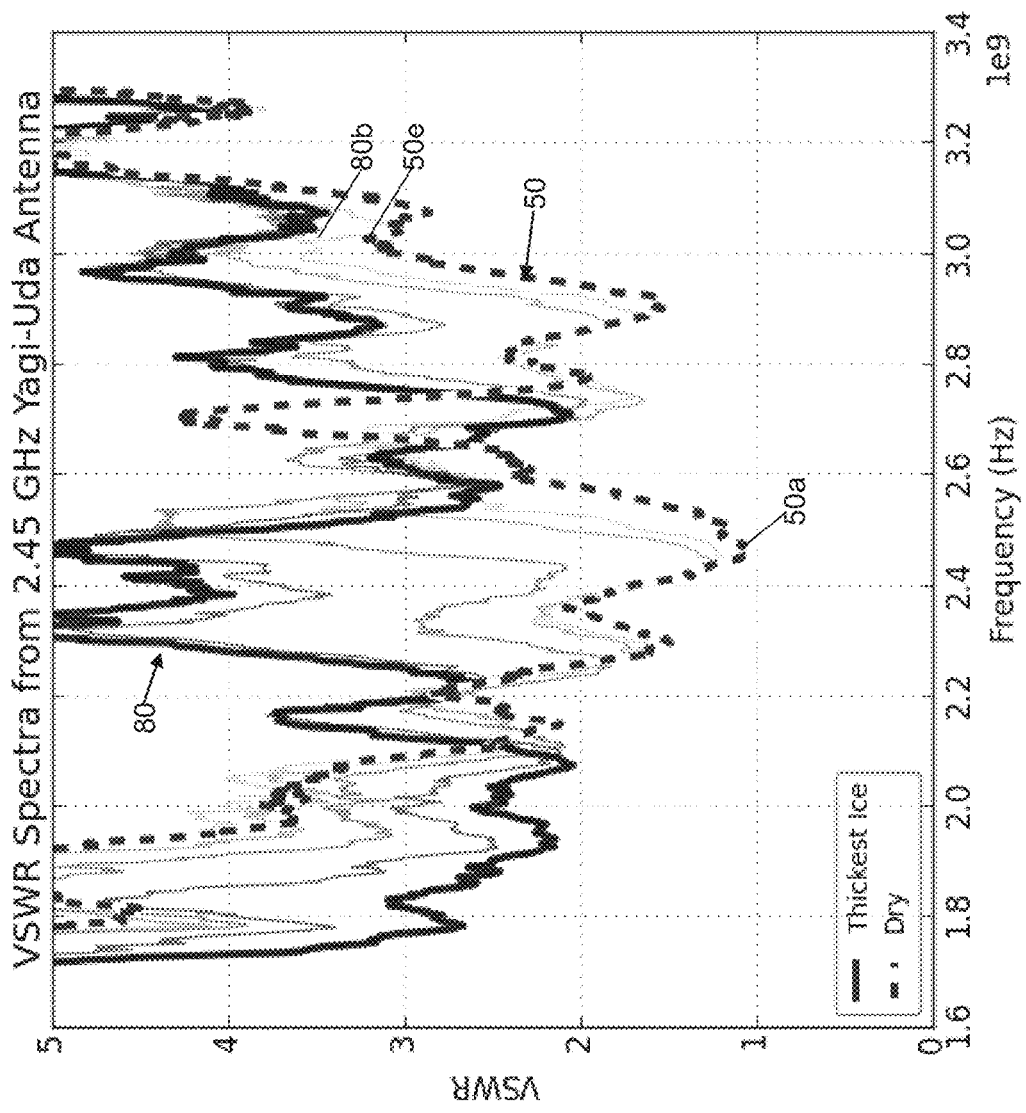
FIG. 7 is a VSWR spectrum for an antenna with a coating of ice arising from freezing rain excited as the thickness of the coating of ice on the antenna increases.
Figure 8:
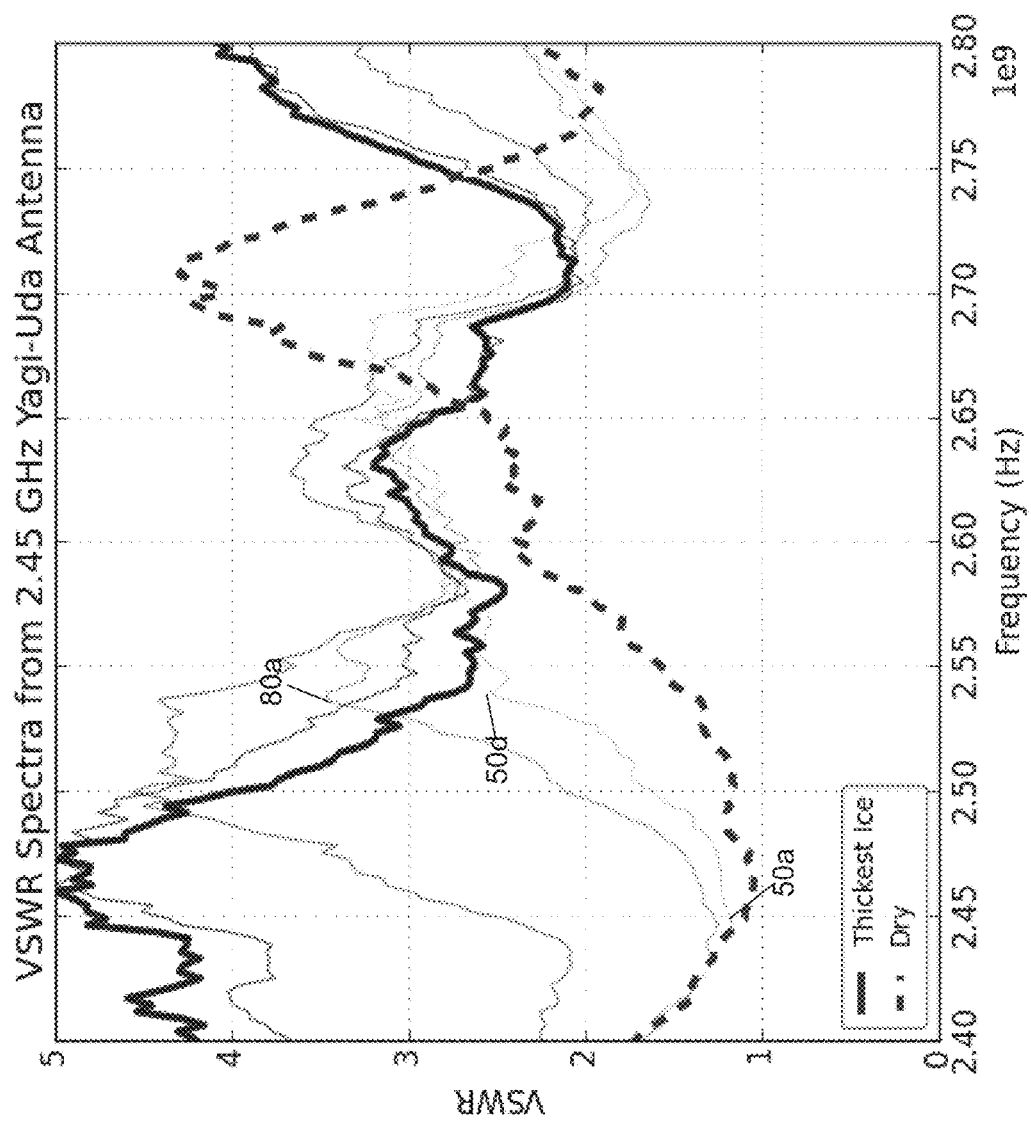
FIG. 8 is a more detailed view of the VSWR spectrum of FIG. 7.

FIG. 7 is an exemplary VSWR spectrum for an antenna of the kind illustrated in FIG. 1 tuned to a resonant frequency of 2.45 GHz when the antenna has coated with ice by applying supercooled droplets of water to the antenna after it has been cooled to approximately −4° C., in order to simulate the effect of freezing rain, and excited by an excitation frequency containing a number of signals having frequencies in the range from approximately 1.7 GHz to approximately 3.3 GHz. The VSWR spectrum of the dry antenna shown in FIG. 2 is also shown at 50 in FIG. 7 for comparison purposes. A number of spectra are shown in FIG. 7 for the antenna as the coating of ice becomes thicker as more layers develop as more supercooled water is applied. The spectrum 80 is for the antenna with the coating of ice at its thickest, corresponding to a radial thickness of ice of around 5 mm.

As can be seen from FIG. 7, the VSWR spectrum for the antenna when coated with ice is different from the VSWR spectrum for the dry antenna, and includes a region, at an input frequency of around 2 GHz, of significantly decreased reflection of input signal power (i.e. reduced VSWR), as compared to the VSWR spectrum for the dry antenna shown in FIG. 2, and a region between around 2.4 and 2.8 GHz (shown in magnified view in FIG. 8) of significant variability in VSWR. As can be seen most clearly in FIG. 8, where the VSWR is at its minimum for the dry antenna at around 2.45 GHz (indicated at 50a in FIGS. 7 and 8), the VSWR for the antenna coated in ice as a result of the supercooled droplets is much greater for all but the thinnest layer of ice. However, even the VSWR spectrum for the thinnest layer of ice can be distinguished from that of the dry antenna, for example by the significant difference between the respective peaks 50d, 80a in the dry antenna VSWR spectrum and the VSWR spectrum for the coated antenna that occur at an input frequency of around 2.55 GHz and by the significant difference between the respective peaks 50e, 80b in the dry antenna VSWR spectrum and the VSWR spectrum for the coated antenna that occur at 3.0 GHz (seen in FIG. 7).

The processing system 16 is configured to analyse the VSWR spectra of the antenna 12 and to identify characteristic features, such as the region of significantly decreased reflection of input signal power at around 2.0 GHz and the VSWR peaks around 2.55 GHz and around 3 GHz, which may be indicative that freezing rain is falling. Having identified that this current condition, the processing system 16 may output an appropriate signal, e.g. to a remote weather station, indicating that ice has been detected.

Again, in order to distinguish between a coating of ice on the antenna caused by freezing rain and a coating of ice caused by a drop in temperature causing a coating of water on the antenna to freeze, the processing system 16 may analyse temperature data from the temperature sensor 20 as well as the VSWR spectra of the antenna. For example, if the data from the sensor 20 indicates that the temperature has not recently dropped to below freezing, the processing system may infer that the coating of ice on the antenna is due to the presence of freezing rain, and may output a signal, e.g. to a remote weather station, indicating that freezing rain been detected. On the other hand, if the coating of ice is accompanied by a recent drop in temperature, the processing system 16 may infer that the coating of ice is a result of the drop in temperature, and may output a signal, e.g. to the remote weather station, indicating that freezing temperatures have been detected.

Figure 9:
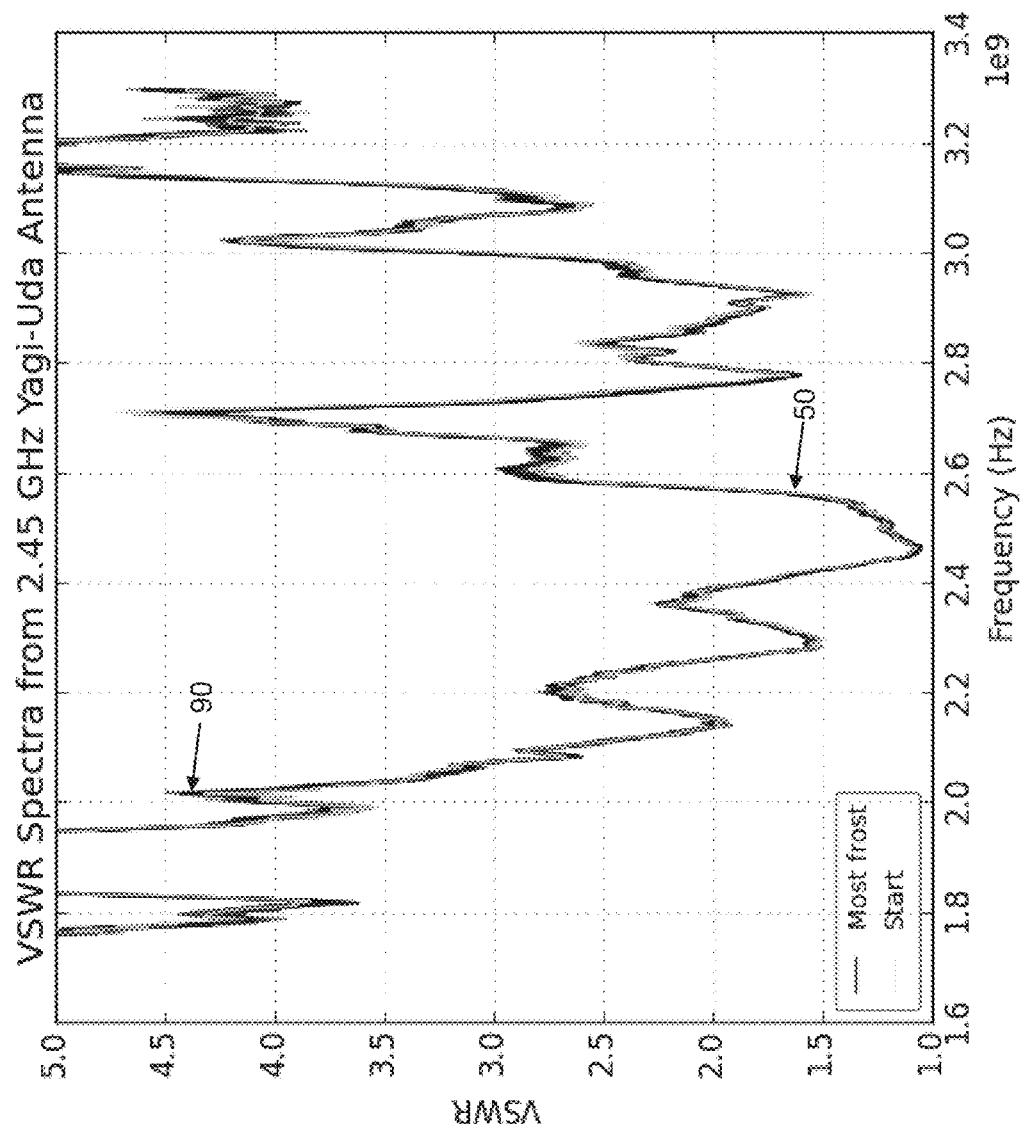
FIG. 9 is a VSWR spectrum for an antenna with a coating of frost as the thickness of the coating of frost on the antenna increases.
Figure 10:
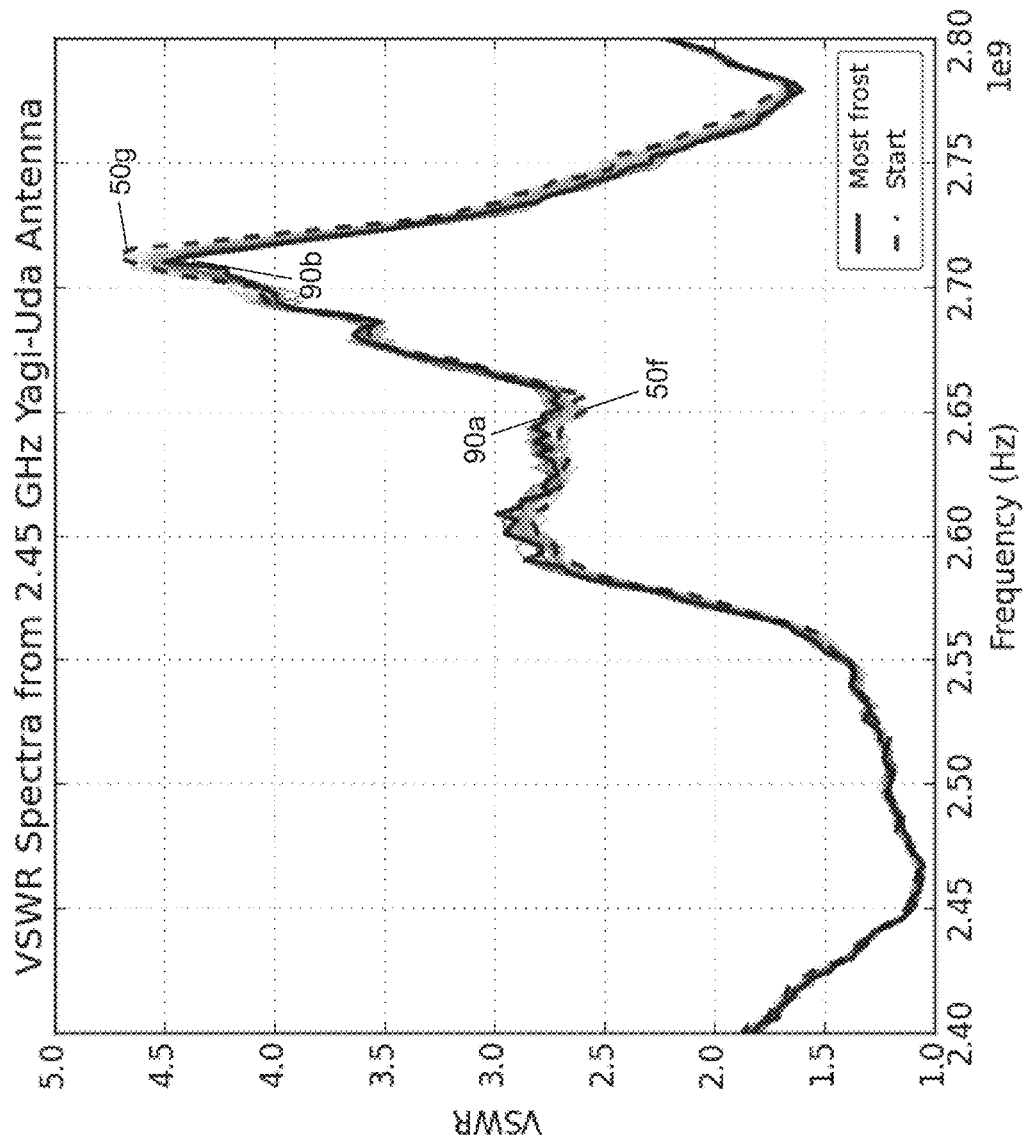
FIG. 10 is a more detailed view of the VSWR spectrum of FIG. 9.

Similar techniques can be used to detect the presence of frost and dew. FIG. 9 is an exemplary VSWR spectrum (shown at 90) for an antenna of the kind illustrated in FIG. 1 tuned to a resonant frequency of 2.45 GHz when the antenna has a coating of frost, and is excited by an excitation frequency containing a number of signals having frequencies in the range from approximately 1.7 GHz to approximately 3.3 GHz. The VSWR spectrum of the dry antenna shown in FIG. 2 is also shown at 50 in FIG. 9 for comparison purposes. FIG. 10 is a magnified view of the spectrum of FIG. 9 for the frequency range 2.40 Ghz to 2.80 GHz. As can be seen from FIGS. 9 and 10, differences exist in the spectrum for the dry antenna and the frosted antenna at input frequencies of around 2.65 GHz (the peaks 50f and 90a respectively in FIG. 10), at input frequencies of around 2.71 GHz (the peaks 50g and 90b respectively) and at input frequencies of around 3.0 GHz (best seen in FIG. 9). Again, the processing system 16 is configured to analyse the VSWR spectra of the antenna 12 and to identify such characteristic features, which may be indicative that frost is present. Having identified that this current condition, the processing system 16 may output an appropriate signal, e.g. to a remote weather station, indicating that frost has been detected.

Figure 11:
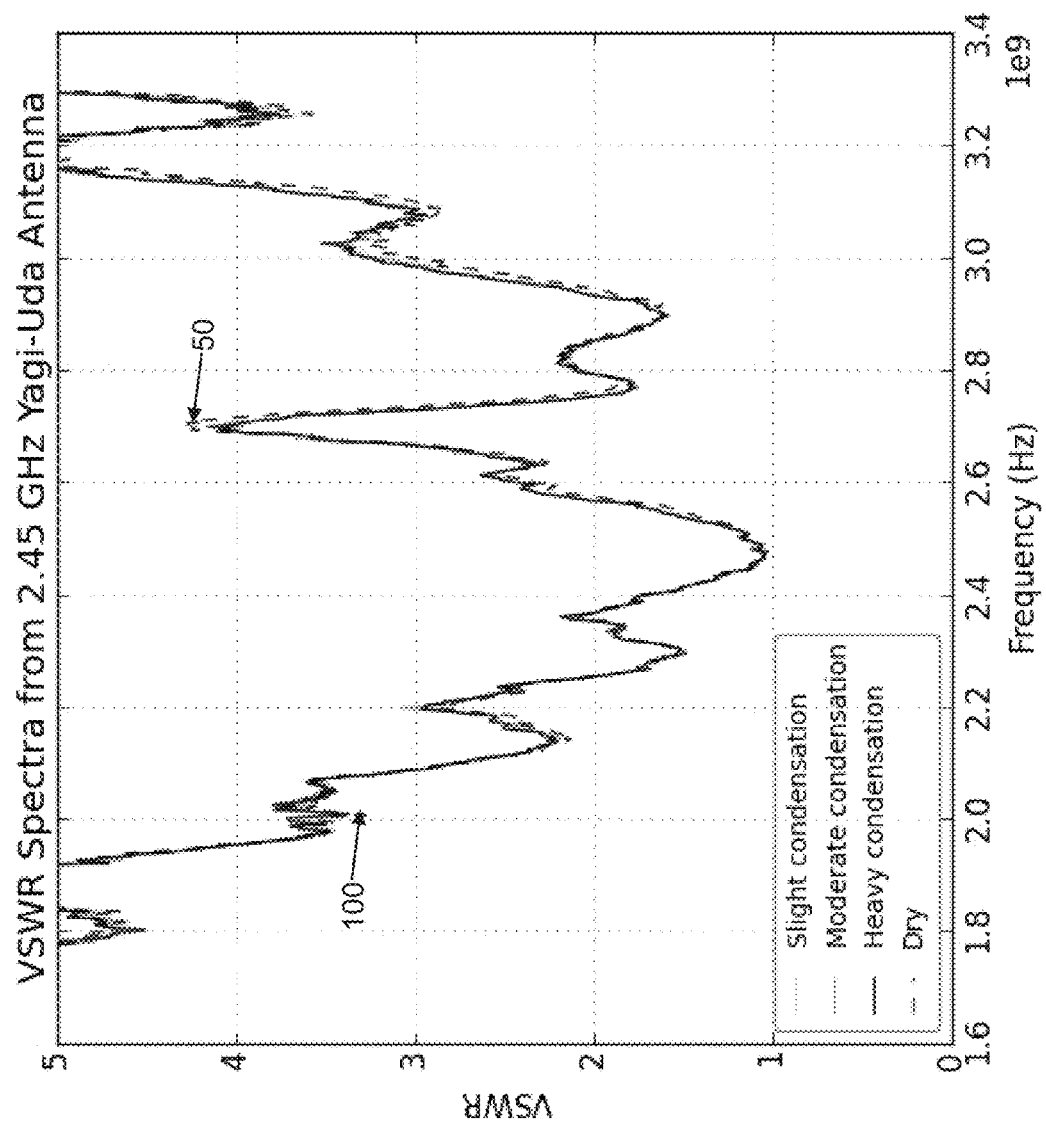
FIG. 11 is a VSWR spectrum for an antenna with a coating of dew or condensation as the amount of dew or condensation on the antenna increases.
Figure 12:
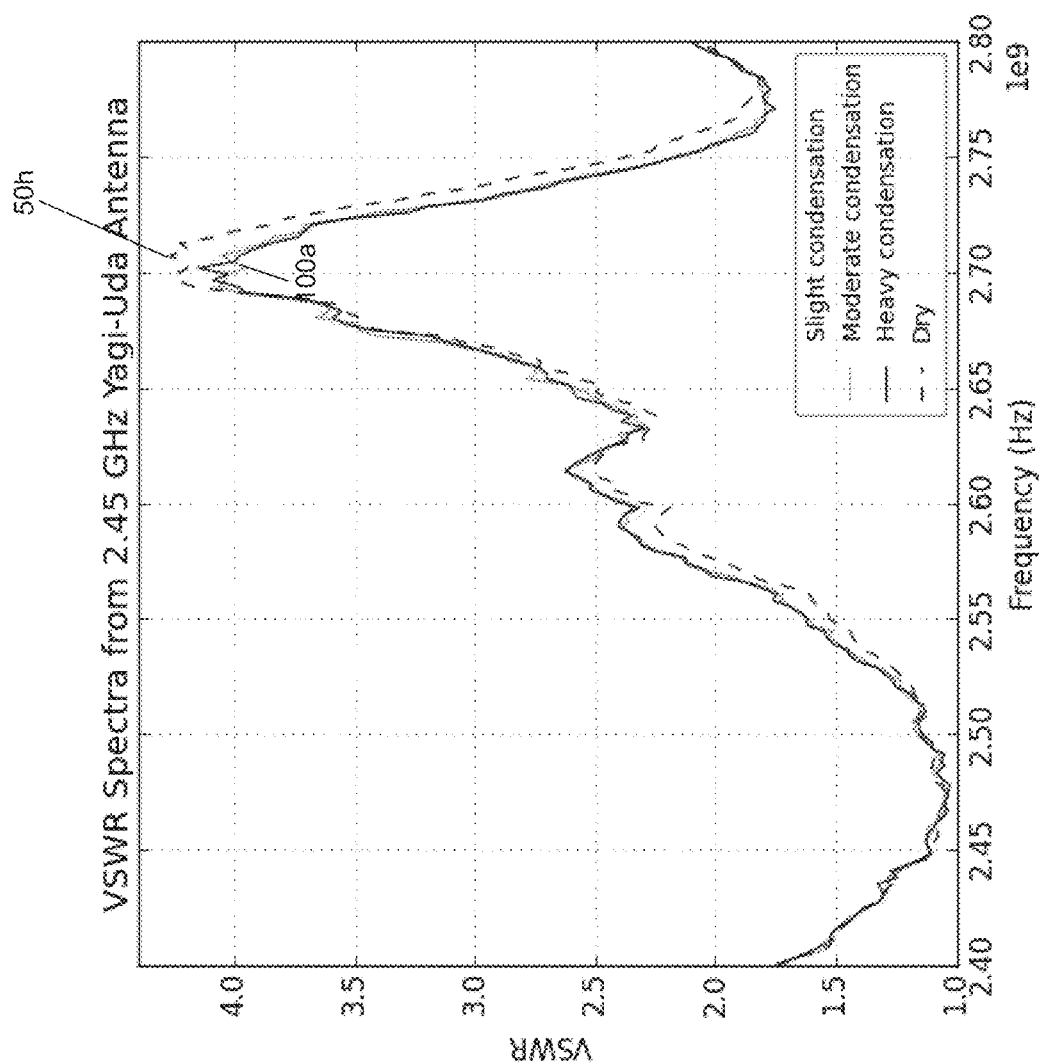
FIG. 12 is a more detailed view of the VSWR spectrum of FIG. 11.

FIG. 11 is an exemplary VSWR spectrum for an antenna of the kind illustrated in FIG. 1 tuned to a resonant frequency of 2.45 GHz when the antenna has a coating of dew or condensation, and is excited by an excitation frequency containing a number of signals having frequencies in the range from approximately 1.8 GHz to approximately 3.3 GHz. The VSWR spectrum of the dry antenna shown in FIG. 2 is also shown at 50 in FIG. 11 for comparison purposes. FIG. 12 is a magnified view of the spectrum of FIG. 11 for the frequency range 2.40 Ghz to 2.80 GHz. As can be seen from FIGS. 11 and 12, differences exist in the spectrum for the dry antenna and the dew/condensation affected antenna at input frequencies of 2.71 GHz (the peaks 50h and 100a respectively) and at input frequencies of around 3.0 GHz (best seen in FIG. 11). Again, the processing system 16 is configured to analyse the VSWR spectra of the antenna 12 and to identify such characteristic features, which may be indicative that dew or condensation is present. Data from the temperature sensor 20 may be used to distinguish between frost and dew if necessary. Having identified this current condition, the processing system 16 may output an appropriate signal, e.g. to a remote weather station, indicating that dew or condensation has been detected.

As will be appreciated, the device 10 can rapidly and accurately detect the presence of a range of precipitation and other meteorological conditions, such as rain, freezing rain, snow, ice, frost and dew, based on the measured reflected power. In addition to detecting current conditions, the device 10 can also measure the rate of change of such conditions, e.g. the rate of accumulation of ice on the antenna 12, by measuring the reflected power at regular intervals. As can be seen from the spectra of FIGS. 2-12, as the amount of water, ice, frost, dew etc. on the antenna 12 increases, the VSWR spectrum of the antenna 12 changes. The processing system 16 may be configured to detect and identify characteristic features of the VSWR spectra over time, and to output a signal indicative of the amount of water, ice etc. on the antenna 12 and/or a signal indicative of the rate of change of water, ice etc. on the antenna 12, to the remote weather station. This data is of course helpful in determining whether conditions are changing (e.g. deteriorating or improving).

In a practical implementation of the device 10, two antennas 12 may be provided, positioned in close proximity to one another, and coupled to the signal generator 14 and the processing system. In this arrangement one of the antennas would be heated by suitable heating means incorporated in the antenna or in the vicinity of the antenna, to act as a reference, whilst the other antenna would not be heated. In this way, improved accuracy of detection of precipitation and other meteorological conditions can be achieved, since the prevailing precipitation or other meteorological conditions will have no (or less) effect on the resonant frequency and input impedance of the second antenna.

In the examples discussed above, the power reflected by the antenna 12 as a result of changes to its resonant frequency arising from the presence of different types of precipitation is measured by measuring VSWR. However, those skilled in the art will appreciate that other parameters such as the input port reflection coefficient $S_{11}$ can be measured to determine the power reflected by the antenna 12, and that characteristic features of the spectra of these parameters can be identified in a manner analogous to the method described above in order to identify precipitation and other meteorological conditions.

Figure 13:
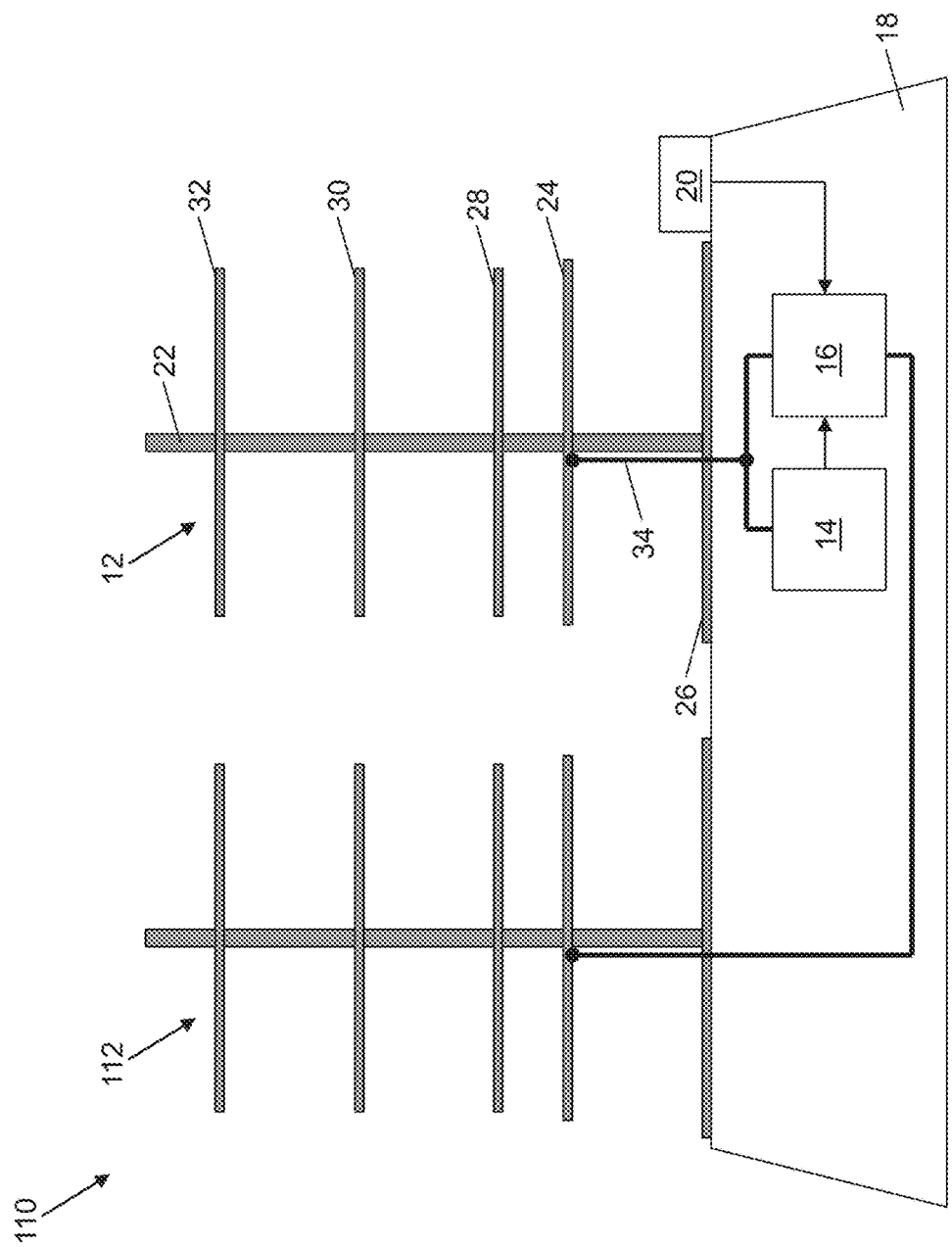
FIG. 13 is a schematic representation of an alternative device for detecting precipitation conditions.

Alternatively or additionally, the power of a signal radiated by the antenna 12 may be measured in order to determine the ability of the antenna 12 to radiate, and thereby detect or confirm the presence of a range of precipitation and other meteorological conditions, such as rain, freezing rain, snow, ice, frost and dew. FIG. 13 is a schematic representation of an exemplary device 110 which can detect the power radiated by the antenna 12.

As can be seen from FIG. 13, the device 110 is similar to the device 10 illustrated in FIG. 1, with the exception that the device 110 includes a second antenna 112 (which may be heated by appropriate heating means incorporated in or in the vicinity of the second antenna as described above), positioned in close proximity to the Yagi-Uda antenna 12. For clarity the second antenna 112 is shown in the schematic representation FIG. 13 as being positioned alongside the antenna 12, but those skilled in the art will appreciate that, given the narrow along-axis sensitivity of a Yagi-Uda antenna, in a practical implementation of the device 110, the second antenna 112 and the Yagi-Uda antenna 12 may be positioned and oriented so as to point towards each other. Moreover, although the second antenna 112 illustrated in the schematic representation of FIG. 13 is depicted as a Yagi-Uda antenna, it is to be understood that the second antenna 112 need not be a Yagi-Uda antenna, but could be an antenna of any suitable type or configuration.

The second antenna 112 is coupled to the processing system 16, such that the power of a signal received by the second antenna 112 as a result of radiation by the first antenna 10 as a result of the excitation signal output by the signal generator 14 can be measured.

The power of the signal received by the second antenna 112 is representative of the power radiated by the antenna 12, and can be compared, by the processing system 16, to the power of the excitation signal output by the signal generator 14 to the antenna 12, in order to estimate the power reflected by the antenna 12. From this estimated reflected power, VSWR spectra of the antenna 12 can be generated and evaluated by the processing system 16, and the presence of different precipitation and other meteorological conditions can be detected using techniques similar to those described above.

Alternatively, the ratio of the power of the signal received by the second antenna 112 to the power of the signal output by the signal generator 14 can be used to estimate the resonant frequency and/or input impedance of the antenna 12. The estimated resonant frequency and/or input impedance of the antenna 12 can then be used by the processing system 16 identify the presence of different precipitation and other meteorological conditions using techniques similar to those described above.

In the examples discussed above excitation signals in the microwave frequency range of approximately 1.7 GHz to approximately 3.0 GHz have been described. This frequency range is advantageous, as it permits the use of a physically small antenna (e.g. an antenna having a length of around 10 cm). Moreover, commercial off the shelf components that operate in this range are readily available, which helps to minimise the bill of materials cost of the device. However, it will be appreciated that other frequency bands may be used where appropriate for particular applications. Thus, the described technology is not limited to the use of excitation signals in the disclosed frequency ranges.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, modules, circuits, and method steps described in connection with the implementations disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the implementations.

The various illustrative blocks, modules, and circuits described in connection with the implementations disclosed herein may be implemented or performed with a general purpose hardware processor, a Digital Signal Processor (DSP), an Application Specified Integrated Circuit (ASIC), a Field Programmable Gate Array (FPGA) or other programmable logic device, discrete gate or transistor logic, discrete hardware components, or any combination thereof designed to perform the functions described herein. A general purpose hardware processor may be a microprocessor, but in the alternative, the hardware processor may be any conventional processor, controller, microcontroller, or state machine. A hardware processor may also be implemented as a combination of computing devices, e.g., a combination of a DSP and a microprocessor, a plurality of microprocessors, one or more microprocessors in conjunction with a DSP core, or any other such configuration.

The steps of a method and functions described in connection with the implementations disclosed herein may be embodied directly in hardware, in a software module executed by a hardware processor, or in a combination of the two. If implemented in software, the functions may be stored on or transmitted as one or more instructions or code on a tangible, non-transitory computer readable medium. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art. A storage medium is coupled to the hardware processor such that the hardware processor can read information from, and write information to, the storage medium. In the alternative, the storage medium may be integral to the hardware processor. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer readable media. The hardware processor and the storage medium may reside in an ASIC.

For purposes of summarizing the disclosure, certain aspects, advantages and novel features s have been described herein. It is to be understood that not necessarily all such advantages may be achieved in accordance with any particular implementation. Thus, the invention may be embodied or carried out in a manner that achieves or optimizes one advantage or group of advantages as taught herein without necessarily achieving other advantages as may be taught or suggested herein.

Various modifications of the above-described implementations will be readily apparent, and the generic principles defined herein may be applied to other implementations without departing from the spirit or scope of the application. Thus, the present application is not intended to be limited to the implementations shown herein but is to be accorded the widest scope consistent with the principles and novel features disclosed herein.

What is claimed is:

1. A device for detecting precipitation conditions, the device comprising:
   a Yagi-Uda antenna tuned a resonant frequency;
   a signal generator coupled to the Yagi-Uda antenna by a transmission line, the signal generator being configured to output an excitation signal to the Yagi-Uda antenna; and
   a processing system coupled to the Yagi-Uda antenna, the processing system being configured to:
      measure the ability of the Yagi-Uda antenna to radiate a signal following excitation of the Yagi-Uda antenna by the excitation signal and, based on the measured ability of the Yadi-Uda antenna, to identify a precipitation or other meteorological condition,
      measure a voltage standing wave ratio (VSWR) in the transmission line in order to measure power reflected by the Yagi-Uda antenna, and
      analyse a VSWR spectrum of the Yagi-Uda antenna and identify characteristic features in the VSWR spectrum to identify a precipitation condition.

2. The device according to claim 1 wherein the signal generator is configured to generate an excitation signal containing a plurality of different signals, each of the plurality of different signals having a different frequency in a frequency range around the resonant frequency of the Yagi-Uda antenna.

3. The device according to claim 1 wherein the signal generator is configured to generate an excitation signal that sweeps or steps through a frequency range around the resonant frequency of the Yagi-Uda antenna.

4. The device according to claim 1 wherein the processing system is configured to identify characteristic features that are indicative of the presence of rain, snow, freezing rain, ice, frost and dew.

5. The device according to claim 1 wherein the processing system is configured to analyse the VSWR spectrum over a period of time and to identify characteristic features of the VSWR spectrum to identity changes in the precipitation condition.

6. The device according claim 1 wherein the excitation signal is an unmodulated signal.

7. The device according to claim 1 wherein the excitation signal has a power in the range of tens of microwatts to tens of milliwatts.

8. The device according to claim 1 further comprising a temperature sensor.

9. The device according to claim 8 wherein the temperature sensor is located within the antenna.

10. A device for detecting precipitation conditions, the device comprising:
    a Yagi-Uda antenna tuned a resonant frequency;
    a signal generator coupled to the Yagi-Uda antenna by a transmission line, the signal generator being configured to output an excitation signal to the Yagi-Uda antenna;
    a processing system coupled to the Yagi-Uda antenna, the processing system being configured to measure the ability of the Yagi-Uda antenna to radiate a signal following excitation of the Yagi-Uda antenna by the excitation signal and, based on the measured ability of the Yadi-Uda antenna, to identify a precipitation or other meteorological condition; and
    a second antenna configured to detect a signal radiated by the Yagi-Uda antenna, wherein the processing system is configured to measure the power of the signal received by the second antenna and, based on the measured received power, to identify a precipitation or other meteorological condition.

11. The device according to claim 10 wherein the second antenna is heated.

* * * * *